(12) United States Patent
Gupta et al.

(10) Patent No.: US 10,786,223 B2
(45) Date of Patent: Sep. 29, 2020

(54) METHOD AND APPARATUS FOR AUTOMATED ULTRASONIC DOPPLER ANGLE AND FLOW VELOCITY ESTIMATION

(75) Inventors: Lalit Gupta, Noida (IN); Ajay Anand, Fishkill, NY (US); John Petruzzello, Carmel, NY (US); Pallavi Vajinepalli, Bangalore (IN); Rajendra Singh Sisodia, Bhopal (IN); Celine Firtion, Surat (IN); Ganesan Ramachandran, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1360 days.

(21) Appl. No.: 14/127,507

(22) PCT Filed: Jun. 29, 2012

(86) PCT No.: PCT/IB2012/053315
§ 371 (c)(1),
(2), (4) Date: Feb. 28, 2014

(87) PCT Pub. No.: WO2013/001503
PCT Pub. Date: Jan. 3, 2013

(65) Prior Publication Data
US 2014/0228688 A1    Aug. 14, 2014

(30) Foreign Application Priority Data
Jun. 30, 2011  (IN) .......................... 2236/CHE/2011

(51) Int. Cl.
*A61B 8/00*  (2006.01)
*A61B 8/06*  (2006.01)
*A61B 8/08*  (2006.01)

(52) U.S. Cl.
CPC .............. *A61B 8/06* (2013.01); *A61B 8/4494* (2013.01); *A61B 8/483* (2013.01); *A61B 8/488* (2013.01); *A61B 8/5223* (2013.01)

(58) Field of Classification Search
CPC ......... A61B 8/06; A61B 8/4494; A61B 8/483; A61B 8/488; A61B 8/5223
See application file for complete search history.

(56) References Cited

U.S. PATENT DOCUMENTS 5,555,886 A    9/1996 Weng et al.
5,606,972 A *  3/1997 Routh ................. G01S 15/8979
                                                  600/455

(Continued)

FOREIGN PATENT DOCUMENTS

EP    1977694 A1    10/2008
JP    2007319203 A   12/2007

(Continued)

OTHER PUBLICATIONS

Ton-Tai Pan et alp; "Spectral Doppler Flow Velocity and Doppler Angle Estimations for Small Vessel by Large Sample Volume", Ultrasonics Symposium, 2001, IEEE vol. 2 Digital Object Indentifier: 10.1109/ULTSYM. 2001.991983, pp. 1401-1402, vol. 2.

(Continued)

Primary Examiner — Christopher L Cook

(57) ABSTRACT

Disclosed is an ultrasound device for measuring blood flow velocity in a blood vessel of a subject without imaging functionality in the device. The measurement depends upon reflections of a collimated beam of ultrasound from a subject's body part. Received electrical signals representative of the reflected ultrasound energy is used for generating a representation of blood flow at a plurality of predetermined locations in the volume and calculating a first blood flow velocity at each of the locations. The representation of flow is used for delineating the blood flow in the blood vessel in (Continued)

the volume. An angle calculating unit calculates the Doppler angle between the direction of the radiated collimated beam in the delineated blood flow at each point. A velocity calculator calculates a second blood flow velocity at the plurality of points based on the calculated first velocities and the calculated angle at the point.

8 Claims, 4 Drawing Sheets

(56) References Cited

U.S. PATENT DOCUMENTS

| | | | |
|---|---|---|---|
| 5,701,898 A | 12/1997 | Adam et al. | |
| 6,322,509 B1* | 11/2001 | Pan | A61B 5/1075 600/443 |
| 6,685,645 B1* | 2/2004 | McLaughlin | A61B 8/08 600/447 |
| 7,534,209 B2 | 5/2009 | Abend et al. | |
| 8,439,840 B1* | 5/2013 | Duffy | A61B 8/483 600/437 |
| 2007/0073153 A1* | 3/2007 | Tortoli | A61B 8/06 600/454 |
| 2008/0009727 A1 | 1/2008 | Kataguchi | |
| 2008/0306386 A1 | 12/2008 | Baba et al. | |
| 2009/0030321 A1* | 1/2009 | Baba | A61B 8/06 600/454 |
| 2009/0292208 A1* | 11/2009 | Jeffrey, Jr. | A61B 5/02007 600/454 |
| 2009/0306513 A1 | 12/2009 | Srinivasan et al. | |
| 2009/0326379 A1 | 12/2009 | Daigle et al. | |
| 2010/0275690 A1* | 11/2010 | Wrobel | A61B 8/06 73/602 |
| 2012/0078106 A1* | 3/2012 | Dentinger | A61B 8/06 600/454 |
| 2012/0215110 A1* | 8/2012 | Wilkening | A61B 8/488 600/453 |

FOREIGN PATENT DOCUMENTS

| | | |
|---|---|---|
| JP | 2009039240 A | 2/2009 |
| WO | 2011058471 A1 | 5/2011 |

OTHER PUBLICATIONS

Ashraf A. Shad et al; "Computer Vision Approach for Ultrasound Doppler Angle Estimation", J Digit Imaging, Dec. 22, 2009, vol. 6, pp. 1-8.

* cited by examiner

METHOD AND APPARATUS FOR AUTOMATED ULTRASONIC DOPPLER ANGLE AND FLOW VELOCITY ESTIMATION

FIELD OF THE INVENTION

This belongs to the field of ultrasound velocimetry.

BACKGROUND OF THE INVENTION

Monitoring a blood flow pattern in the blood vessels of a subject is an important means of assessing the health of the subject. Monitoring blood flow patterns is of importance in maternal and fetal vessels during routine antenatal consultation, carotid artery for stroke screening, lower extremities for Peripheral Arterial Disease (PAD) for example. Especially in the field of obstetrics, measurements of blood flow to the uterus and the fetus is an important means of assessing the adequacy of blood supply to the fetus and hence fetal health or distress.

In ultrasonic velocimetry the velocity of blood flow is measured by the use of Doppler shift experienced by pulsed ultrasound. For the measurement to be accurate, ideally, the beam of ultrasound must be parallel to the blood flow. For measuring the velocity with acceptable accuracy the angle between the direction of flow and the beam, called the Doppler angle, must be below a certain threshold. This threshold is normally 60° and it is not recommended to make measurements when the Doppler angle is greater than this value.

Even when the Doppler angle is less than 60°, the angle needs to be measured and the velocity estimated needs be corrected for the difference between the ideal, i.e. the beam being parallel to the flow, and the actual Doppler angle. When blood velocity is measured using an ultrasound imaging device, it is possible to ascertain that the Doppler angle is within 60° and measure the angle and correct for it. However, ultrasound imaging devices with blood velocimetry are expensive and needs a trained radiologist to operate and interpret the results. Thus there has been a need for inexpensive systems, may be without imaging capabilities, but able to carry out ultrasound blood velocimetry.

SUMMARY OF THE INVENTION

One of the problems encountered in blood velocimetry without imaging is determining the Doppler angle. This document discloses a device for measuring blood flow velocity in the blood vessels of a subject. Such an ultrasound device for measuring blood flow velocity in a blood vessel of a subject, the measurement depending on reflections from a volume of a subject's body part of a collimated beam of ultrasound energy radiated by an ultrasound transducer into the volume of the subject's body part, the device comprising, a signal input unit for receiving electrical signals representative of the reflected ultrasound energy received by each transducer element of an ultrasound transducer including a two dimensional array of transducer elements, an analyzer for analyzing the signals for generating a representation of blood flow at a plurality of predetermined locations in the volume and calculating a first blood flow velocity at each of the locations, a delineating unit for delineating the blood flow in the blood vessel in the volume from the representation of blood flow, an angle calculating unit for calculating an angle between the direction of the radiated collimated beam of ultrasound energy at a plurality of points in the delineated blood flow and the direction of blood flow at the point depending on the delineation and a velocity calculator for calculating a second blood flow velocity at the plurality of points based on the calculated first velocities at the plurality of locations and the calculated angle at the point for conveying the second blood velocity to a user.

Such a device provides a means of carrying blood velocimetry in a subject wherein the device has no imaging function. This may provide the advantage that such a device is more economical than a device with imaging functionality. This may further provide the advantage that a user who is not a highly trained ultrasonologist may also carry out blood velocimetry.

Further, a method of measuring blood flow velocity using Doppler ultrasound is disclosed. A method of determining a Doppler angle for Doppler blood velocimetry in a volume of a body part of a subject, the method comprising the steps of, a receiving step of receiving electrical signals from a two dimensional array of ultrasound transducers, the signals being representative of ultrasound energy reflected from the body part of the subject, the ultrasound energy having been radiated by the two dimensional array, a computation step of computing the Doppler power in a predetermined frequency band received from predetermined locations in the volume, a generating step of generating a first three dimensional array wherein each cell of the array contains the Doppler power value received from a location in the volume with a predefined relationship between the location and the position of the cell in the array, a mapping step of generating a second three dimensional array wherein each cell of the second array contains a binary bit representing whether a the value in the corresponding cell of the first three dimensional array is above a threshold or not, an identification step of identifying a group of adjoining cells that contain the binary bit representing values above the threshold, in each two dimensional array forming the second three dimensional array, a calculation step of calculating the three dimensional coordinates of the centroid of the area covered by each group in each of the two dimensional arrays and an angle calculation step of calculating the angle between a first line joining two centroids nearest to each other in the two adjacent two dimensional arrays and a second line passing through one of the two centroids, the line being parallel to the radiated ultrasound.

With this, the angle between the beam of ultrasound and the blood vessel is known and may be used to correct measured values of blood velocity in a known way. This enables a method of carrying out blood velocimetry without the need for a device with imaging capability. It is to be understood that the method may also be used in a device with imaging capability also to correct the measured values of blood flow velocity, using the Doppler angle calculated using the method.

BRIEF DESCRIPTION OF THE DRAWINGS

These and other aspects will be described in detail, by way of example, on the basis of the following embodiments and implementations, with reference to the accompanying drawings, wherein.

DETAILED DESCRIPTION OF EMBODIMENTS

Figure 1:
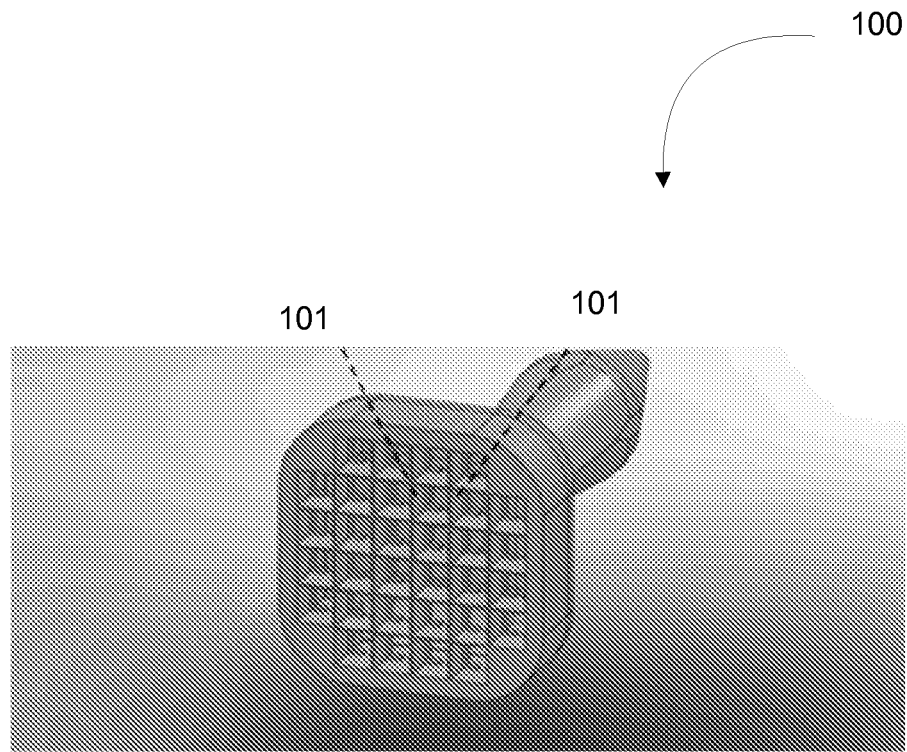
FIG. 1 is a two dimensional array of Ultrasound transducer elements.

FIG. 1 shows an ultrasound transducer 100 that is used with the disclosed device and the arrangement of transducer elements therein. The transducer arrangement consists of a plurality of transducer elements arranged in a two dimensional array. The FIG. 1 shows a 32 element transducer arranged in six rows. The rows at the top and bottom of the array have four elements each and there are four rows of six elements each between them. However, this is only an exemplary arrangement and other arrangements may also be used. It is also possible that the size of the transducer elements and their shape may be different. A characteristic of the transducer array is that the individual transducer elements are activated independently of one another and are not driven to steer the beam with phase shifted signals. Such an array as the one in FIG. 1 may be driven to produce a collimated beam of ultrasound in a known way. During Doppler data acquisition, the elements may be driven either sequentially or in groups such that the acoustic signal from one transducer does not affect the others that are driven at the same time.

Figure 2:
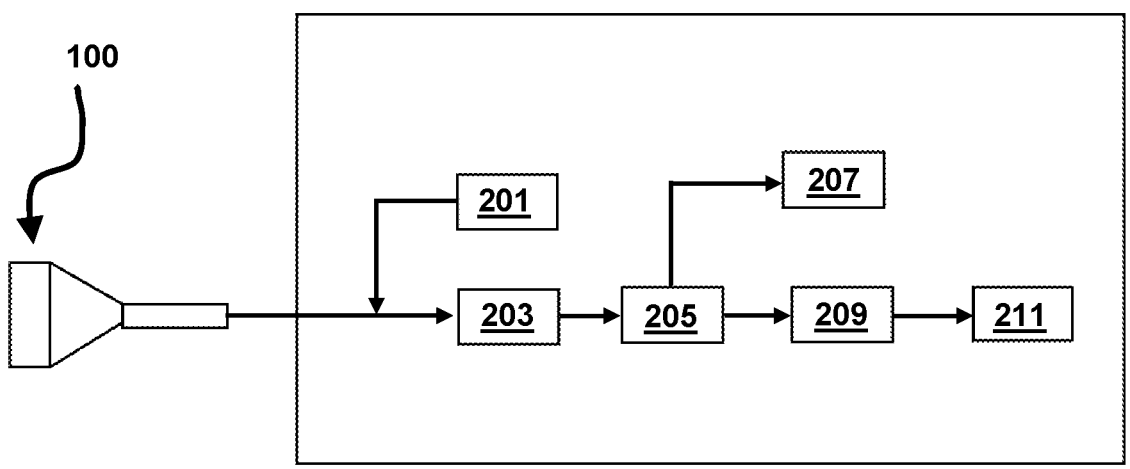
FIG. 2 is an embodiment of the disclosed device.

FIG. 2 shows the disclosed device 200 schematically. The elements of the transducers are driven, as described before with reference to FIG. 1, by the driver 201. The transducers receive the reflected ultrasound energy and convert them to electrical signals. The signals provided by the individual transducer elements are analyzed by the analyzer 203 to compute the Doppler power at a known number of points in the sample volume and stores them in a three dimensional array. An angle determining unit 207 uses this three dimensional array to determine the angle, at each point of the sample volume from which Doppler data has been acquired, between the ultrasound radiation at the point and the direction of the vessel at the point. The angles thus calculated are the Doppler angles at each point in the sample volume. A Doppler velocity calculator 209 uses the Doppler data and the determined angle to determine the velocity of blood flow at all points at which the Doppler angle is less than 60°.

The blood flow velocities, corrected for the Doppler angle are conveyed to the user suitably using the user interface 211. It is to be understood that the user interface itself need not be a part of the device and may be an external unit to which the calculated velocities are sent in a wired or wireless means for being conveyed suitably to the user. This could for instance be a printer or a general purpose computer or a mobile device. However, it may be more useful to have the user interface as a part of the device itself so that the device is a stand-alone unit that needs no interaction with other devices or systems.

It is possible that due to the anatomy of the vessels in an individual subject or the position of the transducer on the subject or both, none of the calculated Doppler angles are below 60° or that at very few points in the sample volume are the Doppler angles less than 60°. The device may be configured to convey to the user, in such cases, that the position of the transducer on the subject be changed for useful measurement to be made.

A method of determining the Doppler angle during Doppler blood velocimetry is also disclosed hereby. This describes the method of processing the reflected ultrasound energy pulses received and converted to electrical signals by a transducer. The transducer has a sparse array of transducer elements as described with reference to FIG. 1 and the disclosed device above.

The received signal is processed for Doppler power. The frequency range chosen for this is 300-2500 Hz, which is, typically, representative of blood flow. The Doppler data is acquired from points in the scan volume at step lengths of 2 mm, for example, from each element of the transducer, in a direction perpendicular to the surface of the transducer elements. Doppler data may be acquired at any chosen step lengths and 2 mm is normally deemed sufficient since, usually, no vessel of interest is smaller than 2 mm in diameter. Doppler data is acquired up to a distance of 10 cm from the transducer or the skin surface of the subject or any other suitable starting and ending point. The analyzed data is used to generate a three dimensional representation of flow in the scan volume.

It is to be understood that the numerical values above are mentioned for the sake of explanation. However, it is possible to vary these values to suit a particular application. Or that the devices are built based on this disclosure, which have a varying values and ranges to make the device applicable in cases in which the values are different from those stated. For instance the frequency range may be wider to accommodate the measurement of a larger blood velocity caused by a stenosis. Or that the step lengths smaller than 2 mm—in case of infants which may have blood vessels of a much smaller cross sectional diameter, and so on. All such variations are deemed to be covered under the scope of this disclosure.

For the further description, it is assumed that the step length chosen is in fact 2 mm and that the transducer is a 32 element transducer as described before. Further, each transducer element face is assumed to be a square with the dimensions 10 mm by 10 mm. With this, the flow information that results may be arranged in a is a 3 dimensional array which has 6 rows, 6 columns and 50 layers, except for the top and bottom rows, which have only 4 transducer elements. Thus, the four corner cells of each layer will have no Doppler power information in them. Except for the said cells, each cell of this array contains information in terms of Doppler power measured. This data is used to create a second array that is a replica of the first array in structure but has a digital '1' in all those cells that have a Doppler power value greater than a predetermined threshold and a digital '0' in all those cells that have a Doppler power value less than or equal to that threshold. The threshold is chosen such that noise and spurious signals do not interfere with the delineation of the vessels.

This three dimensional array is visualized as the flow map in three dimensions from which the vessels in the sample volume are delineated. That means, the three dimensional array may be visualised as having dimensions in the real world matching the volume of the subject's body from which the reflected radiation is received and processed. Thus each cell of the array has the dimensions corresponding to the dimensions of the radiating surface of the transducer elements and the distance between layers is visualised to have the step lengths at which the Doppler power is received and processed. This visualisation of the array as having physical dimensions is key to the disclosure.

In each layer of the array all neighbouring cells containing a '1' are considered to belong to the same vessel. This group of cells containing adjoining 1's are deemed to represent the cross section of a vessel in a plane formed by each layer.

Thus we get cross sections of the vessels separated by distances of 2 mm in the direction of the layers of the array.

Once the sections are determined, the centroid of each of them is determined in a known way. Starting from any layer, the nearest centroids on the two adjacent layers are treated as belonging to the same vessel. Thus a line joining all such centroids is deemed to be the centre line of each of the vessels in the sample volume. Once these vessels are thus delineated, the vessel is treated as piecewise linear and the angle between each line joining two nearest centroids and a line at each centroid perpendicular to the section and in the direction of the transducer may be determined in a known way. Each of these angles so measured is the Doppler angle at that point.

The smallest angle determined, i.e., a point at the centre of the cross section of the vessel at which the ultrasound beam is closest to being parallel to the vessel is extracted and the Doppler power information from the first three dimensional array belonging to the cell closest to the centroid is used to calculate the velocity information using the formula:

$$v = \frac{Fs * c}{2 * Ft * \cos(th)}$$

wherein, v denotes the velocity of blood flow in an artery at a particular point, Fs represents the Doppler frequency shift, c represents speed of sound in the medium, th represents the angle between the probe and the vessel and Ft represents the frequency of the probe.

It is possible that due to the position of the transducer on the surface of the abdomen of the subject, and the path of the vessel relative to the transducer, none of the Doppler angles calculated as described above has a value less than 60°. In one variant of the method, an information that the position of the probe needs to be changed, since the current position is not suitable for velocimetry with sufficient accuracy, may be conveyed to the user, in such cases. The number of locations where the calculated angle is less than the predetermined threshold is counted and, the number is compared with a predetermined number. If the counted number is less than the predetermined number the information may be conveyed to the user suitably to change the position of the transducer on the surface of the subject's body. It is to be understood that the word position here may mean the location on the subject, the angle or tilt and orientation and so on. Needless to say, the process may be repeated till reliable values of the velocity of blood flow are determined i.e., at least one Doppler angle value less than 60° is obtained.

In another variant of the method, the velocities of blood flow at different points on the vessel that meet the criteria, viz., where the Doppler angle is less than 60°, may be calculated and the attention of the user may be suitably drawn to any large difference between them. A large difference in velocities may be indicative of an obstruction in the vessel or a hemorrhage.

It is also conceivable that the Doppler data for all the cells adjacent to the centroid are used to calculate the velocities at each of those cells and the average of the velocities may be obtained to determine the blood flow velocity and then corrected for the Doppler angle. Alternatively, the average of values stored in all the cells adjacent to the centroid is first determined and using this average, the velocity is determined and then corrected for the Doppler angle.

Figure 3A:
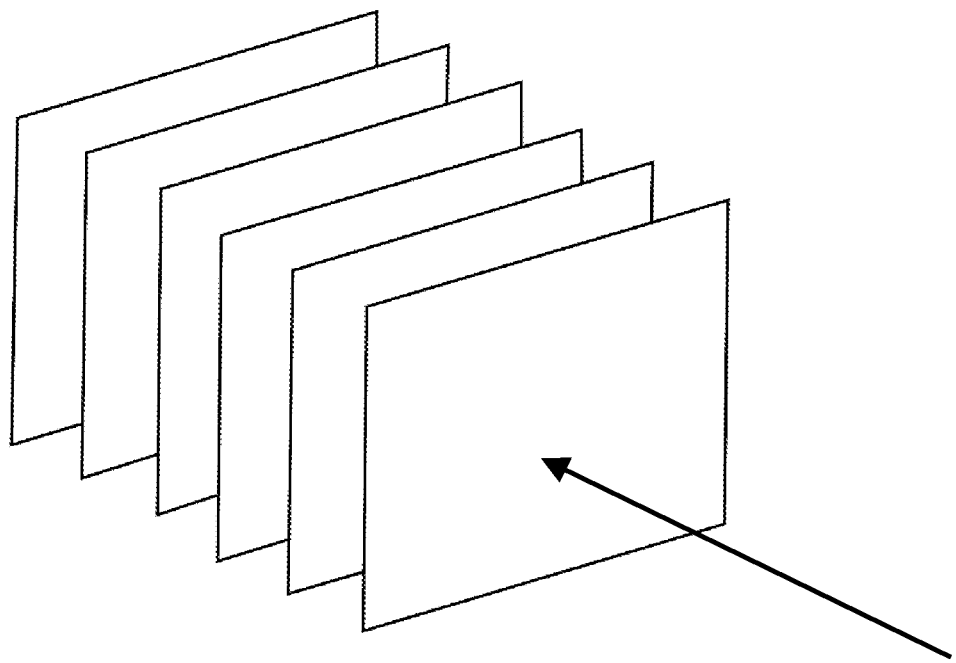
FIG. 3a is a representation of an aspect of the disclosed method.
Figure 3B:
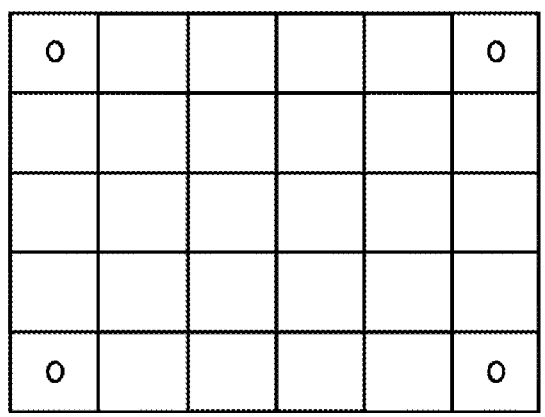
FIG. 3b is a representation of an aspect of the disclosed method
Figure 3C:
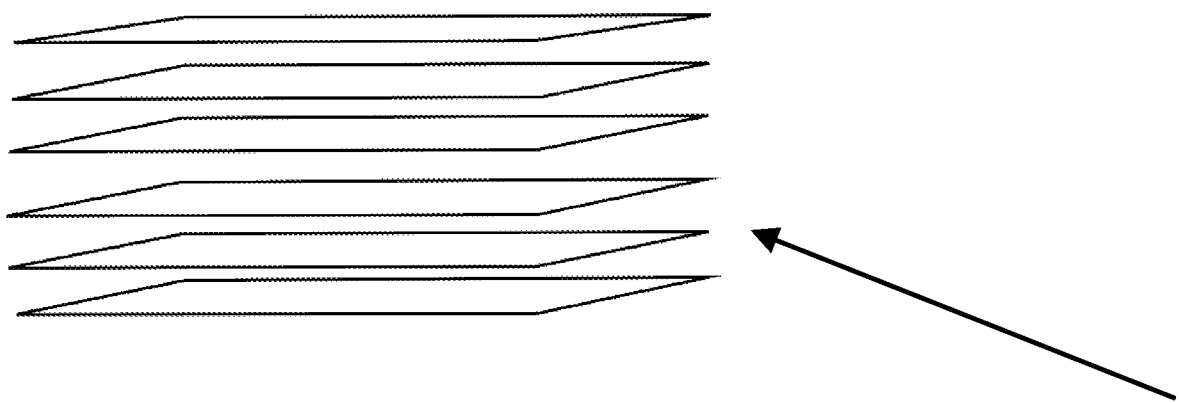
FIG. 3c is a representation of an aspect of the disclosed method.
Figure 3D:
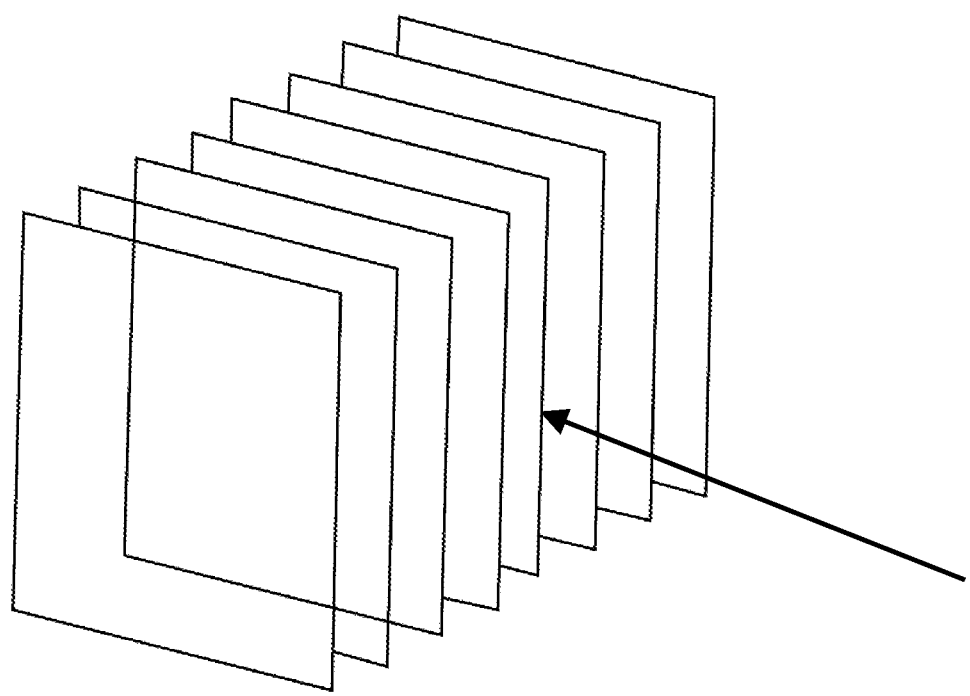
FIG. 3d is a representation of an aspect of the disclosed method; in which, like reference numerals refer to like parts in the different figures.

The description hitherto is with the assumption that the sections are obtained and the flow mapped at the layers of the array as shown in FIG. 3a. The visualisation of the array, for purposes of understanding, is shown in 3b. It is to be understood that this is not the only way of delineating the vessels. It is equally possible to do it with the other two planes perpendicular to the one shown in 3a. These are indicated in FIG. 3b and in FIG. 3c with suitable modifications in the calculations that follow. Knowing the normal anatomy of the vessels being considered for velocimetry and the position of the probe it may be advantageous to choose one of the three possibilities. In all the three figures, the arrow indicates the direction of insonation or radiation of the collimated beam of Ultrasound.

The description hitherto has assumed that the vessel structures are always distinct enough to delineate the vessels uniquely based on the method described. However in reality it is possible that the vessels are twisted or cross over each other such that the vessels when delineated based on the method described will at some point cross over. In other words the flow is mapped for one vessel for a certain distance (certain number of contiguous centroids) and then a centroid belonging to another vessel is treated as the next contiguous centroid. Thus once the centroids are determined and the flow is mapped, the Doppler data stored in the array are compared in a known way to determine if they actually belong to the same vessel or not. The comparison may be based on cross correlation or any other numerical comparison method. An alternative may be to use the Cross Teager-Ville distribution or cross Wigner-Ville distributions, for instance. The blood flow has characteristics that remain substantially the same along a given blood vessel. By comparing these characteristics at different points in the vessel it may be confirmed that the mapping of the vessels has been carried out correctly. In case this test shows that the mapping is incorrect, by repositioning the transducer better results could easily be obtained.

While the embodiments have been described in detail in the drawings and description, such drawings and description are to be considered exemplary and not restrictive; the invention is not limited to the disclosed embodiments.

For example, it is possible to practice the invention in an arrangement wherein there are more than one computer memory units to store the three dimensional arrays. Similarly, the steps of methods disclosed in different embodiments may be combined with advantage.

Other variations to the disclosed embodiments can be understood and effected by those skilled in the art, in practicing the claimed invention, from a study of the drawings, the disclosure, and the appended claims. In the claims, the word "comprising" does not exclude elements or steps other than those mentioned, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The invention claimed is:

1. An ultrasound device configured to measure blood flow velocity in a blood vessel of a subject, the ultrasound device comprising:
   an ultrasound transducer comprising transducer elements configured to:
      radiate a collimated beam of ultrasound energy; and
      receive reflected ultrasound energy; and a processor configured to:
analyze electrical signals representative of the reflected ultrasound energy to generate a representation of blood flow at a plurality of predetermined locations in a volume of the subject's body;
calculate a first blood flow velocity at each of the plurality of predetermined locations;
delineate the blood flow in the blood vessel in the volume based on the representation of the blood flow;
calculate a plurality of angles between a direction of the collimated beam of ultrasound energy at a plurality of points in the delineated blood flow and a direction of the blood flow at the plurality of points wherein calculating the angles further comprises:
determining centroids of the blood vessel at the plurality of points,
determining a centerline of the blood vessel between the centroids, and
calculating the plurality of angles based on the centerline of the blood vessel;
calculate a second blood flow velocity at each of the plurality of points based on the calculated first blood flow velocities at the plurality of locations and a single calculated angle at a given point;
compare values of the second blood flow velocities at the plurality of points to one another;
responsive to a difference between one of the first blood flow velocities or one of the second blood flow velocities and at least one other velocity of the first blood flow velocities and the second blood flow velocities indicating an obstruction or a hemorrhage of the blood vessel;
generate an indication of the difference for communication to a user, wherein the processor is programmed to determine a smallest angle of the calculated plurality of angles to determine the second blood flow velocity at any point based on the smallest angle, the smallest angle corresponding to a location at a center of a cross section of the blood vessel at which the collimated beam of ultrasound energy is closest to being parallel to the centerline of the blood vessel.

2. The ultrasound device of claim 1, wherein the second blood flow velocity at any point is determined only after the calculated angle at that point is less than a predetermined value.

3. The ultrasound device of claim 2, wherein the processor is configured to convey to the user information indicating the user should change a position of the ultrasound transducer on the subject when a number of the calculated angles that are below the predetermined value is less than a predefined number.

4. The ultrasound device of claim 1, where the processor is configured such that the second blood flow velocity at any point is further determined based on each of a speed of sound of blood in the blood vessel, the smallest angle, and a frequency of the ultrasound transducer.

5. The ultrasound device of claim 1, wherein the ultrasound device has no imaging functionality.

6. An ultrasound device for measuring blood flow velocity in a blood vessel of a subject, the ultrasound device comprising:
an ultrasound transducer comprising a two dimensional array of transducer elements, the ultrasound transducer configured to:
radiate a collimated beam of ultrasound energy into a volume of a subject's body part, thereby generating reflected ultrasound energy, and
output electrical signals representative of the reflected ultrasound energy received by each transducer element of the ultrasound transducer; and
a processor configured to:
analyze the electrical signals to generate a three-dimensional array, wherein the three-dimensional array has row and column dimensions corresponding to the two dimensional array of transducer elements and a layer dimension corresponding to a direction of the radiated collimated beam of ultrasound energy;
calculate power values at the cells of the three-dimensional array based on the electrical signals representative of the reflected ultrasound energy received by the transducer elements of the ultrasound transducer;
generate a replica three-dimensional array corresponding to the three-dimensional array, the cells of the replica three-dimensional array having binary values indicative of whether the cells correspond to blood vessels, the binary values being determined by thresholding the power values of the corresponding cells of the three-dimensional array;
delineate blood vessels in the replica three-dimensional array;
calculate angles between the delineated blood vessels and the direction of the radiated collimated beam of ultrasound energy;
calculate one or more blood flow velocities using the angles and power values of the cells of the three-dimensional array; and
convey the one or more blood flow velocities to a user.

7. The ultrasound device of claim 6, wherein the processor is further configured to:
delineate the blood vessels in the replica three-dimensional array by identifying blood vessel centroids in layers of the replica three-dimensional array as contiguous groups of cells of the replica three-dimensional array having binary values indicative of blood vessels, and
connect the centroids across the layers.

8. The ultrasound device of claim 6, wherein the ultrasound device has no imaging functionality and the individual transducer elements of the two dimensional transducer array are activated independently of one another and are not driven to steer the beam with phase shifted signals.

* * * * *